United States Patent
Haas et al.

(10) Patent No.: US 6,838,572 B2
(45) Date of Patent: Jan. 4, 2005

(54) PROCESS FOR THE EPOXIDATION OF OLEFINS

(75) Inventors: Thomas Haas, Frankfurt (DE); Claudia Brasse, Hanau (DE); Guido Stochniol, Gelnhausen (DE); Willi Hofen, Rodenbach (DE); Wolfgang Wöll, Maintal-Doernighelm (DE); Georg Thiele, Hanau (DE)

(73) Assignees: Degussa AG, Düsseldorf (DE); Uhde GmbH, Dortmund (DE)

( * ) Notice: Subject to any disclaimer, the term of this patent is extended or adjusted under 35 U.S.C. 154(b) by 0 days.

(21) Appl. No.: 10/669,993

(22) Filed: Sep. 24, 2003

(65) Prior Publication Data

US 2004/0127730 A1 Jul. 1, 2004

Related U.S. Application Data

(60) Provisional application No. 60/414,327, filed on Sep. 30, 2002, and provisional application No. 60/414,329, filed on Sep. 30, 2002.

(51) Int. Cl.[7] .............................................. C07D 301/12
(52) U.S. Cl. ...................... 549/531; 549/524; 549/529
(58) Field of Search ................................ 549/524, 529, 549/531

(56) References Cited

U.S. PATENT DOCUMENTS

| | | | |
|---|---|---|---|
| 2,870,171 A | 1/1959 | Gable | |
| 4,410,501 A | 10/1983 | Taramasso et al. | |
| 4,833,260 A | 5/1989 | Neri et al. | |
| 4,999,179 A | 3/1991 | Sugihara et al. | |
| 5,523,426 A | 6/1996 | Jubin, Jr. et al. | |
| 5,591,875 A | 1/1997 | Chang et al. | |
| 5,599,955 A | 2/1997 | Vora et al. | |
| 5,620,935 A | 4/1997 | Thiele | |
| 5,675,026 A | 10/1997 | Thiele | |
| 5,760,253 A | 6/1998 | Danner et al. | |
| 5,849,937 A | 12/1998 | Jubin, Jr. et al. | |
| 5,849,938 A | 12/1998 | Reuter et al. | |
| 5,912,367 A | 6/1999 | Chang | |
| 6,042,807 A | 3/2000 | Faraj | |
| 6,063,941 A | 5/2000 | Gilbeau | |
| 6,372,924 B2 | 4/2002 | Thiele | |
| 6,429,322 B1 | 8/2002 | Catinat et al. | |

FOREIGN PATENT DOCUMENTS

| | | |
|---|---|---|
| DE | 196 23 611 | 12/1997 |
| DE | 197 23 950 | 12/1998 |
| DE | 197 54 185 | 2/1999 |
| DE | 198 35 907 | 2/2000 |
| DE | 199 38 547 | 2/2001 |
| DE | 100 26 363 | 11/2001 |
| EP | 0 100 118 | 2/1984 |
| EP | 0 100 119 | 2/1984 |
| EP | 0 133 510 | 2/1985 |
| EP | 0 230 349 | 7/1987 |
| EP | 0 230 949 | 8/1987 |
| EP | 0 425 893 | 5/1991 |
| EP | 0 568 336 | 11/1993 |
| EP | 0 588 337 | 11/1993 |
| EP | 0 583 828 | 2/1994 |
| EP | 0 645 473 | 3/1995 |
| EP | 0 659 473 | 6/1995 |
| EP | 0 712 852 | 5/1996 |
| EP | 0 719 768 | 7/1996 |
| EP | 0 757 043 | 2/1997 |
| EP | 0 757 045 | 2/1997 |
| EP | 0 795 537 | 9/1997 |
| EP | 0 827 785 | 3/1998 |
| EP | 0 930 308 | 7/1999 |
| EP | 0 936 219 | 8/1999 |
| EP | 0 940 393 | 9/1999 |
| EP | 1 072 599 | 1/2001 |
| EP | 1 072 600 | 1/2001 |
| EP | 1 122 248 | 8/2001 |
| EP | 1 138 387 | 10/2001 |
| EP | 1 167 290 | 1/2002 |
| EP | 1 221 442 | 7/2002 |
| FR | 2 810 981 | 1/2002 |
| JP | 216636 | 6/1990 |
| WO | WO 97/47613 | 12/1997 |
| WO | WO 97/47614 | 12/1997 |
| WO | WO 98/47845 | 10/1998 |
| WO | WO 99/01445 | 1/1999 |
| WO | WO 99/07690 | 2/1999 |
| WO | WO 99/11639 | 3/1999 |
| WO | WO 00/07695 | 2/2000 |
| WO | WO 00/17178 | 3/2000 |
| WO | WO 00/25881 | 5/2000 |
| WO | WO 00/76989 | 12/2000 |
| WO | WO 01/57012 | 8/2001 |
| WO | WO 01/92242 | 12/2001 |
| WO | WO 02/02545 | 1/2002 |

*Primary Examiner*—Amelia A. Owens
(74) *Attorney, Agent, or Firm*—Smith, Gambrell & Russell, LLP

(57) ABSTRACT

A continuous process for the epoxidation of olefins with hydrogen peroxide in the presence of a heterogeneous catalyst promoting the epoxidation reaction, whereby the aqueous reaction mixture contains i) an olefin; ii) hydrogen peroxide; iii) less than 100 wppm of alkali metals, earth alkali metals, both irrespective whether in ionic, complex or covalently bonded form, bases or cations of bases having a $pk_B$ of less than 4.5, or combinations thereof; and, iv) at least 100 wppm of bases or cations of bases having a $pk_B$ of at least 4.5 or combinations thereof, whereby the wppm are based on the total weight of hydrogen peroxide in the reaction mixture.

38 Claims, No Drawings

PROCESS FOR THE EPOXIDATION OF OLEFINS

REFERENCE TO A RELATED APPLICATION

This application claims the benefit of our copending provisional application 60/414,329 filed Sep. 30, 2002 which is relied on and incorporated herein by reference, and claims benefit of provisional application 60/414,327 filed Sep. 30, 2002.

INTRODUCTION

The present invention relates to an improved continuous process for the epoxidation of olefins using a heterogeneous catalyst for promoting the epoxidation reaction, whereby deactivation of the catalyst has been considerably reduced.

BACKGROUND OF THE INVENTION

From EP-A 100 119 it is known that propene can be converted by hydrogen peroxide into propene oxide if a titanium-containing zeolite is used as catalyst.

Unreacted hydrogen peroxide cannot be recovered economically from the epoxidation reaction mixture. Furthermore, unreacted hydrogen peroxide involves additional effort and expenditure in the working up of the reaction mixture. The epoxidation of olefin is therefore preferably carried out with an excess of olefin and up to a high hydrogen peroxide conversion. In order to achieve a high hydrogen peroxide conversion it is advantageous to use a continuous flow reaction system. Furthermore, high selectivity for the desired olefin oxide is important for an industrial scale process to achieve high yields and to reduce costs for subsequent work-up.

However, activity and selectivity of the above described titanium-containing zeolite catalysts are sharply reduced over time in a continuous process for the epoxidation of olefins, making frequent catalyst regeneration necessary. For an industrial scale process, this is not acceptable for economic reasons.

In the literature numerous routes to either increase catalyst activity and/or selectivity or to reduce catalyst deactivation for the above described titanium-containing zeolite catalysts are described:

For example, from EP-A 230 949, it is known to neutralize the titanium silicalite catalyst either prior to its use in an epoxidation reaction or in situ with strong bases thereby introducing large amounts of alkali metal or alkaline-earth metal ions into the reaction mixture. This neutralization resulted in an increase in activity and selectivity to form the desired olefin oxide in a batch process.

The experiments in EP-A 757 043, however, show that in a continuous process the activity is considerably reduced, if the catalyst is neutralized prior to or during the reaction. Therefore, it is suggested to treat the catalyst prior to or during the epoxidation reaction with a neutral or acidic salt. The experimental data in EP-A 757 043 confirm that by addition of neutral or acidic salts the selectivity is increased but the activity is less reduced compared to the addition of a base. But EP-A 757 043 only shows examples wherein the catalyst is treated with the salt prior to the reaction and the catalyst is used in slurry form. Additionally the experiments were only run for 8 hours but nevertheless show a dramatic drop in catalyst activity only after 4 hours which is by no means acceptable for an industrial process.

Similarly EP-A 712 852 teaches that by performing an epoxidation process catalyzed by titanium silicalite in the presence of a non-basic salt the selectivity is increases. All the examples are run in batch operation mode with a stirred catalyst slurry for one hour. Although it can be confirmed that the presence of non-basic salts may have a positive influence on catalyst selectivity in a short term experiment, it was discovered that even if non-basic salts are present in a reaction mixture for a continuous epoxidation reaction the activity and selectivity drops dramatically over time. Thus the teaching of EP-A 712 852 does not lead to a reaction system that can be economically employed in a continuous epoxidation process using hydrogen peroxide in presence of a heterogeneous catalyst.

Several patent documents deal with the problem of optimizing activity and selectivity of titanium silicalite catalyst in epoxidation reactions by means of addition of nitrogen containing compounds and pH-adjustment of the reaction mixture. For example EP-A 1 072 599 teaches the addition of nitrogen containing bases to the reaction mixture, whereas EP-A 1 072 600 discloses the use of a buffer system comprising salts of those nitrogen containing bases for pH adjustment. EP-A 940 393 relates to the addition of amide group containing organic compounds to the epoxidation reaction mixture. U.S. Pat. No. 6,429,322 discloses the addition of strong bases like alkali or alkaline earth metal or tetraalkyl ammonium hydroxide and the addition of weak bases like ammonium hydroxide or alkali or alkaline earth metal salts of weak acids for pH adjustment of the reaction mixture. But in none of these references is the effect of impurities commonly present in commercially available aqueous hydrogen peroxide solution on the long term activity and selectivity of the titanium silicalite catalyst addressed or investigated.

Today, the vast majority of hydrogen peroxide is produced by the well-known anthraquinone process. A survey of the anthraquinone process and its numerous modifications is given in G. Goor, J. Glenneberg, S. Jacobi: "Hydrogen Peroxide" Ullmann's Encyclopedia of Industrial Chemistry, Electronic Release, $6^{th}$ ed. Wiley-VCH, Weinheim Jun. 2000, page 14.

Crude hydrogen peroxide solutions or concentrated hydrogen peroxide solutions obtained from the anthraquinone process contain a plurality of compounds in addition to hydrogen peroxide in low concentrations. These compounds are either impurities or additives like stabilizers. The impurities are compounds that are extracted from the working solution into the aqueous phase. They are mainly ionic or polar species like carboxylic acids, alcohols, carbonyl compounds and amines. These impurities are therefore also found in commercial hydrogen peroxide solutions.

For example, hydroquinone solvents that are commonly used in the above described process are nitrogen containing compounds like amides and ureas (see Ullmann, supra, page 6). Particularly preferred are tetraalkyl ureas like tetrabutyl urea. The use of these solvents result in amine impurities like monoalkyl or dialkyl, especially monobutyl and dibutyl, amines in the final hydrogen peroxide solutions. For example the commercial hydrogen peroxide solution HYPROX® available from Degussa AG contains up to 200 wppm mono- and dibutyl amine based on the weight of hydrogen peroxide.

In WO 00/76989 the influence of ionic components in commercially available aqueous hydrogen peroxide solutions that are used in epoxidation reactions as described in the above prior art documents is discussed. Ionic components, especially phosphates and nitrates, are added to commercially available aqueous hydrogen peroxide solutions as stabilizers to reduce hazardous decomposition of hydrogen peroxide. WO 00/76989 teaches contrary to the disclosure in the above prior art documents that the presence of ionic components in the reaction mixture, even those that have been added as stabilizers to commercial hydrogen peroxide, are detrimental to the long term selectivity in a continuous titanium silicalite catalyzed epoxidation reaction and should therefore be reduced to a minimum. Contrary to the above prior art documents, continuous reactions running up to 300 hours were conducted showing that if ionic components are present in an amount of more than 100 ppm the long term selectivity is reduced. To solve this problem, it is suggested to remove ionic components from hydrogen peroxide solutions prior to use in epoxidation reactions by means of ion exchangers. Moreover, WO 00/76989 teaches that ammonium compounds and ammonia should be avoided under any circumstances since these compounds may lead to undesired side products by oxirane ring opening reactions with the formed olefin oxide. Although the teaching in WO 00/76989 leads to some improvement in long term selectivity compared to the above prior publication, this improvement is still insufficient for an industrial scale process. Furthermore, this improvement can be achieved only with the complicated and, both in terms of investment and process costs, economically undesirable additional process step of ion exchange. Last but not least, removal of stabilizing ions like phosphate and nitrate from the hydrogen peroxide solution makes the process more hazardous and additional measures have to be taken to ensure safety during the entire process.

Contradicting the teaching of WO 00/76989, WO 01/57012 discloses that the use of crude hydrogen peroxide solutions directly obtained from the anthraquinone process having large amounts of, for example, sodium, nitrate, phosphate, and organic impurities, is superior with respect to product selectivity compared to highly purified hydrogen peroxide solutions comprising very low amounts of sodium, nitrate, and phosphate. The experiments, however, were only conducted for a few hours so that the long term activity and selectivity of the catalyst cannot be determined from that reference.

Again, another approach is shown in WO 01/92242, wherein a titanium silicalite catalyzed process for epoxidation of olefins using crude hydrogen peroxide solutions in the presence of a compound having aminocarbonyl functionality in which the nitrogen bears at least one hydrogen atom is disclosed. The examples show a batch type process that is conducted up to a conversion of hydrogen peroxide of 85%. After two hours, the reaction is terminated even if the conversion of 85% has not been reached. Although the experimental data show an improvement with respect to the reaction rate compared to compounds with aminocarbonyl functionality having no hydrogen atom bonded to the nitrogen atom long term activity and selectivity of the catalyst in a continuous process is not determinable from the information in WO 01/92242.

DE-A 199 36 547 discloses a continuous titanium silicalite catalyzed process for epoxidation of olefins with hydrogen peroxide whereby the conversion is kept constant by increase of reaction temperature and adjusting the pH of the reaction mixture. In a long term experiment (1000 hours), it could be verified that by adjusting the pH the increase in temperature and the rate of increase could be reduced compared to an experiment without pH adjustment. But conversion and selectivity were the same irrespective whether the pH was adjusted or not.

Thus, an object of the present invention is to provide a continuous process for the epoxidation of olefins with hydrogen peroxide in the presence of a heterogeneous catalyst promoting the epoxidation reaction whereby an improvement in long term activity and selectivity of the catalyst compared to the above discussed prior art can be achieved without adding additional process steps and in an economic way.

SUMMARY OF THE INVENTION

In carrying out the present invention, a continuous process for the epoxidation of olefins with hydrogen peroxide is conducted in the presence of a heterogeneous catalyst promoting the epoxidation reaction, whereby the aqueous reaction mixture comprises:

i) an olefin;

ii) hydrogen peroxide;

iii) less than 100 wppm of alkali metals, earth alkali metals, both irrespective whether in ionic or complex form, bases or cations of bases having a $pk_B$ of less than 4.5, or combinations thereof; and iv) at least 100 wppm of bases or cations of bases having a $pk_B$ of at least 4.5 or combinations thereof, whereby the wppm are based on the total weight of hydrogen peroxide in the reaction mixture.

DETAILED DESCRIPTION OF THE INVENTION

It has been surprisingly discovered that, even when taking into account the content of ionic components in aqueous hydrogen peroxide solutions, these solutions can be used in the process of the present invention without further purification like ion exchange, if a hydrogen peroxide solution is selected for the process resulting in less than 100 wppm of alkali metals, earth alkali metals, both irrespective whether in ionic or complex form, bases or cations of bases having a $pk_B$ of less than 4.5, or combinations thereof based on the total weight of hydrogen peroxide in the reaction mixture. A content of anions irrespective of their nature above 100 wppm based on the total weight of hydrogen peroxide in the reaction mixture is not detrimental for the long term activity and selectivity of the catalyst as long as the reaction mixture contains at least 100 wppm of bases or cations of bases having a $pk_B$ of at least 4.5 or combinations thereof based on the total weight of hydrogen peroxide in the reaction mixture.

Thus, contrary to the teaching of the prior art, neither the use of crude hydrogen peroxide solutions obtained from the anthraquinone process without carefully controlling the amount of alkali metals and amines having a $pk_B$ below 4.5, nor the use of purified hydrogen peroxide solutions, where in addition to the metal cations also the stabilizing anions have been removed, are suitable for an economic process for epoxidation of olefins.

The process of the present invention surprisingly results in a long term selectivity of 90% at a hydrogen peroxide conversion of well above 90% even after running the process for more than 2300 hours. This result has been achieved without any expensive purification steps like ion exchange.

Preferably the reaction mixture further comprises:

v) at least 100 wppm anions or compounds that, can dissociate to form anions in total based on the weight of hydrogen peroxide.

It is a particular advantage of the present hydrogen peroxide solution that anions can be present in the usual stabilizing amounts. These stabilizing anions are preferably any kind of oxophosphorous anions like orthophosphate, hydrogen phosphate, dihydrogen phosphate, pyrophosphate, nitrate.

These stabilizing anions, or compounds that can dissociate in the hydrogen peroxide solution to produce these stabilizing anions, are preferably present in an amount of at most 1000 wppm, preferably 100–1000 wppm, more preferred 200–800 wppm, most preferred 200–600 wppm, based on the weight of hydrogen peroxide.

According to a preferred embodiment of the present invention the amount of components of group iii) in total is less than 80 wppm, preferably less than 70 wppm, more preferably less than 60 wppm and most preferably less than 50 wppm based on the total weight of hydrogen peroxide.

It is particularly advantageous if the reaction mixture comprises:
  iiia) less than 50 wppm alkali metals, alkaline earth metals or combinations thereof in total, irrespective whether the alkali or alkaline earth metals are present in cationic or complex form; and
  iiib) less than 50 wppm of amines having a $pk_B$ of less than 4.5 or the corresponding protonated compounds in total;
  where the wppm are based on the weight of hydrogen peroxide.

It is preferred to reduce the amount of alkali metals, alkaline earth metals or combinations thereof in total, irrespective whether the alkali or alkaline earth metals are present in cationic or complex form to be less than 40 wppm, more preferred less than 35 wppm, in order to further improve the long term activity and selectivity of the catalyst.

The effect of the presence of such amines is even more pronounced than the effect of the alkali or alkaline earth metals. Therefore, it is particularly preferred to reduce the amount of amines having a $pk_B$ of less than 4.5 in the aqueous hydrogen peroxide solution in total to less than 40 wppm, preferably less than 30 wppm, more preferred less than 20 wppm, and most preferred less than 10 wppm, based on the weight of hydrogen peroxide in the solution.

It is another surprising result of the present invention that the presence of bases or cations of bases having a $pk_B$ of less 4.5 like trimethylamine ($pK_B$=4.26) or methylamine ($pk_B$= 3.36) are detrimental for the long term activity and selectivity of the catalyst whereas the presence of bases or cations of bases having a $pk_B$ of at least 4.5 like ammonia ($pk_B$= 4.76) are mandatory in order to achieve the desired result. This fundamental difference in behavior of quite similar compounds was not foreseeable in light of the prior art.

Especially detrimental to the activity and selectivity of the epoxidation catalyst is the presence of alkyl amines, especially secondary and tertiary alkyl amines.

Furthermore it is preferred, if the amount of components of group iv) in total is 3000 wppm at most and is preferably from 150 to 2000 wppm, more preferably from 200 to 1500 wppm, most preferably from 300 to 1200 wppm based on the weight of hydrogen peroxide.

According to a particularly preferred embodiment of the present invention the components of group iv) are selected from organic amines and amides having a $pk_B$ of at least 4.5, organic hydroxylamines having a $pk_B$ of at least 4.5, ammonia and hydroxylamine. Preferably no aminocarbonyl functional compounds are added to the reaction mixture.

The hydrogen peroxide is used in the process according to the invention in the form of an aqueous solution with a hydrogen peroxide content of 1 to 90 wt. %, preferably 10 to 70 wt. %. A solution having 50 to 70 wt. % hydrogen peroxide is particularly preferably resulting in even more improved long term activity and selectivity of the employed catalyst.

For the process of the present invention an aqueous hydrogen peroxide solution can be used that is obtained by a process for the preparation of the hydrogen peroxide solution according to the anthraquinone loop process comprising:
  (a) hydrogenation of a working solution comprising an organic solvent or mixture of organic solvents and one or more active anthraquinone compounds,
  (b) oxidation of the resulting hydrogenated working solution to form hydrogen peroxide,
  (c) extraction of hydrogen peroxide with water,
  (d) stabilizing of the resulting extracted aqueous hydrogen peroxide solution,
  (e) optionally concentrating the aqueous hydrogen peroxide solution to a concentration of hydrogen peroxide of at least 50% by weight based on the weight of the hydrogen peroxide solution,
  (f) drying of the working solution after extraction, and
  (g) regeneration and purification of the working solution,
  whereby during the entire process neither alkali or alkaline earth metals nor amines having a $pk_B$ of less than 4.5 or compounds forming such amines during the process are introduced in amounts that result in amounts of
    iii) 100 wppm or more of alkali metals, earth alkali metals, both irrespective whether in ionic or complex form, bases or cations of bases having a $pk_B$ of less than 4.5, or combinations thereof;
  preferably
    iiia) 50 wppm or more of alkali metals, alkaline earth metals or combinations thereof in total, irrespective whether the alkali or alkaline earth metals are present in cationic or complex form; or
    iiib) 50 wppm or more of amines having a $pk_B$ of less than 4.5 or the corresponding protonated compounds in total;
  in the resulting aqueous hydrogen peroxide solution, whereby the wppm are based on the weight of hydrogen peroxide.

Another advantage of the hydrogen peroxide solution that can be used in the process of the present invention is that it can be easily produced in an economic way employing the well-known anthraquinone process, whereby additional purification steps are not necessary and are preferably not applied when preparing the hydrogen peroxide solution to be used in the process of the present invention. The only requirement for the process the hydrogen peroxide solution compared to the known modifications of the anthraquinone process is that the process has to be carefully controlled to avoid introduction of alkali metals, alkaline earth metals, amines having a $pk_B$ of less than 4.5, or compounds that may form during the anthraquinone process such amines during the preparation of the hydrogen peroxide solution in amounts that would result in concentrations above the limits specified according to the present invention.

Although many variations of the anthraquinone process to achieve this requirement are conceivable, it is particularly preferred to use a working solution that is essentially free of organic nitrogen compounds, to dry the working solution in above step (f) without using alkali or alkaline earth metal compounds that are in the anthraquinone process of the prior art commonly employed for drying, and to regenerate the working solution in step (g) by treating with active aluminum oxide. Preferably, drying is conducted by water evaporation in vacuum.

The process of the present invention is particularly advantageous if the catalytic epoxidation is performed in a continuous flow reaction system, wherein the reaction mixture is passed through a fixed catalyst bed in down-flow operation mode and the reaction heat is at least partially removed during the course of the reaction. The process of the present invention is therefore preferably conducted in a fixed bed reactor comprising cooling means of the type well known in the art.

A particularly preferred embodiment of the present invention refers to a process for the catalytic epoxidation of propene with hydrogen peroxide in a continuous flow reaction system conduct ed in a multiphase reaction mixture comprising a liquid aqueous hydrogen peroxide rich phase containing methanol and an liquid organic propene rich phase, wherein the reaction mixture is passed through a fixed catalyst bed in down-flow operation mode and the reaction heat is at least partially removed during the course of the reaction.

The present inventors have surprisingly discovered, contrary to the general textbook knowledge as exemplified by A. Gianetto, "Multiphase Reactors: Types, Characteristics and Uses", in Multiphase Chemical Reactors: Theory, Design, Scale-up, Hemisphere Publishing Corporation, 1986, that a cooled fixed bed reactor can be successfully operated in a down-flow operation to increase product selectivity and thereby overall product yield compared to an up-flow operation as previously used in the prior art. This effect is even more surprising since it is known that the epoxidations of olefin is a highly exothermic reaction that is difficult to control since this reaction has a considerably high activation temperature and therefore has to be conducted at a certain minimum temperature to achieve economically reasonable conversion. But on the other hand the heat generated by the exothermic reaction has to be effectively re moved from the reactor since at increased temperatures unwanted side reactions take place with the result that product selectivity is decreased. The effect of limited temperature, increase within the catalyst bed is discussed to some extent in EP-A-659 473. With respect to the examples it is disclosed that in conventional tubular reactors temperature rise in the catalyst bed exceeds 15° C. whereas according to the examples in EP-A-659 473 the temperature rise is 8° C. at most and in the preferred embodiment 5½° C. Thus according to the teaching of EP-A-659 473 only temperature rise within the catalyst bed has to be kept as low as possible in order to achieve high yields of propylene oxide. This reduced temperature rise could be achieved according to EP-A-659 473 only by conducting the reaction in a single reaction zone to only a partial conversion with the result that the majority of the reaction mixture has to be recycled, and by intermediately cooling the reaction mixture.

According to the teaching of A. Gianetto, et al., when operating a conventional tubular fixed bed reactor poor heat dissipation and nonuniform temperature within the catalyst bed has to be expected in case of downflow operation mode. Thus, it has to be expected that by using a downflow operation mode in a conventional cooled fixed bed reactor without intermediate external cooling of the reaction mixture a high temperature rise within the catalyst bed due to poor heat dissipation would occur that should dramatically decrease product selectivity and thus the yield. But, contrary to this expectation, as will be shown in more detail below in the examples, better product selectivity at the same conversion compared to up-flow operation mode is achieved and similar or even better overall yields based on hydrogen peroxide compared to the most preferred embodiments in EP-A-659 473 are obtainable although a conventional reactor system without intermediate external cooling was used.

In the practice of the present invention any reactor having a fixed catalyst bed and cooling means can be used. Adiabatic reaction conditions as taught in EP-A 659 473 and U.S. Pat. No. 5,849,937 should be avoided. Preferably, tubular, multi-tubular or multi-plate reactors, which are all well known in the art, are used. Most preferably, tubular reactors having a cooling jacket are used since they are standardly available at relatively low cost. As cooling medium that is pumped through the cooling means, preferably the cooling jacket, all standard cooling media like oils, alcohols, liquid salts or water can be used. Water is most preferred.

The process according to the invention for the epoxidation of olefins, preferably propene, is typically carried out at a temperature of 30° to 80° C., preferably at 40° to 60° C. According to a preferred embodiment of the present invention, the temperature profile within the reactor is maintained such that the cooling medium temperature of the cooling means of the tubular reactor is at least 40° C. and the maximum temperature within the catalyst bed is 60° C. at the most, preferably 55° C. Preferably, the temperature of the cooling medium is controlled by a thermostat.

The maximum temperature within the catalyst bed is measured with a plurality of suitable temperature measurement means like thermocouples or a Pt-100 arranged approximately along the axis of the preferably tubular reactor at suitable distances with respect to each other. The number, position within the reactor and distances between the temperature measurement means are adjusted to measure the temperature of the catalyst bed within the entire reactor as exact as necessary.

The maximum temperature of the catalyst bed can be adjusted by different means. Depending on the selected reactor type, the maximum temperature of the catalyst bed can be adjusted by controlling the flow rate of the reaction mixture passing through the reactor, by controlling the flow rate of the cooling medium passing through the cooling means or by lowering the catalyst activity, for instance by diluting the catalyst with inert material.

The flow rate of the cooling medium is preferably adjusted to keep the temperature difference between entry of the cooling medium into the cooling means and exit below 5° C., preferably below 3° C., most preferably 2° C.

By selecting such a narrowly defined temperature profile within the reactor an optimized balance between hydrogen peroxide conversion and olefin oxide selectivity can be achieved.

The pressure within the reactor is usually maintained at 5 to 50 bar preferably 15 to 30 bar.

According to a preferred embodiment, the reaction mixture is passed through the catalyst bed with a superficial velocity from 1 to 100 m/h, preferably 5 to 50 m/h, most preferably 5 to 30 m/h. The superficial velocity is defined as the ratio of volume flow rate/cross section of the catalyst bed. Consequently, the superficial velocity can be varied in a given reactor by adjusting the flow rate of the reaction mixture.

Additionally, it is preferred to pass the reaction mixture through the catalyst bed with a liquid hourly space velocity (LHSV) from 1 to 20 $h^{-1}$, preferably 1.3 to 15 $h^{-1}$.

Whenever the flow rate of the reaction mixture is adjusted to fulfill the above-defined requirements for superficial velocity and liquid hourly space velocity particularly high selectivity can be achieved.

According to particularly preferred embodiment of the present invention, the process is conducted to maintain the catalyst bed in a trickle bed state. It has been surprisingly discovered that if the trickle bed state is maintained under certain flow conditions the effect of the present invention i.e. the increased propene oxide selectivity will be particularly pronounced.

These conditions are as follows:

$G/\lambda < 2000$ m/h and $L\psi < 50$ m/h, wherein

G is the gaseous superficial velocity defined as the gaseous flow rate in m³/h in the continuous flow reactor divided by the cross-section of the catalyst bed in m².

L is the liquid superficial velocity defined as the liquid flow rate in m³/h in the continuous flow reactor divided by the cross-section of the catalyst bed in m², $$\lambda = \left[\left(\frac{\rho_G}{\rho_W}\right)\left(\frac{\rho_L}{\rho_{Air}}\right)\right]^{1/2}, \text{ and } \psi = \left(\frac{\sigma_W}{\sigma_L}\right) \cdot \left[\left(\frac{\mu_L}{\mu_W}\right)\left(\frac{\rho_W}{\rho_L}\right)^2\right]^{1/3}$$

$\rho_G$ is the density of the gaseous phase in g/cm²

$\rho_L$ is the density of the liquid phase in g/cm³, $\rho_W$ is the density of water in g/cm³, $\rho_{Air}$ is the density of air in g/cm³, $\sigma_W$ is the surface tension of water in dyn/cm, $\sigma_L$ is the surface tension of the liquid phase in dyn/cm, $\mu_L$ is the viscosity of the liquid phase in centipoise, $\mu_W$ is the viscosity of water in centipoise.

In order to be able to operate the process continuously when changing and/or regenerating the epoxidation catalyst, two or more flow reactors may if desired also be operated in parallel or in series in the before-described manner.

Crystalline, titanium-containing zeolites especially those of the composition $(TiO_2)_x(SiO_2)_{1-x}$ where x is from 0.001 to 0.05 and having a MFI or MEL crystalline structure, known as titanium silicalite-1 and titanium silicalite-2, are suitable as catalysts for the epoxidation process according to the invention. Such catalysts may be produced for example according to the process described in U.S. Pat. No. 4,410,501. The titanium silicalite catalyst may be employed as a shaped catalyst in the form of granules, extrudates or shaped bodies. For the forming process the catalyst may contain 1 to 99% of a binder or carrier material, all binders and carrier materials being suitable that do not react with hydrogen peroxide or with the epoxide under the reaction conditions employed for the epoxidation. Extrudates with a diameter of 1 to 5 mm are preferably used as fixed bed catalysts.

When practicing the present invention it is preferred that the overall feed stream to the reactor comprises an aqueous hydrogen peroxide solution, an olefin and an organic solvent. In this way these components may be introduced into the reactor as independent feeds or one or more of these feeds are mixed prior to introduction into the reactor.

Using the process according to the invention any olefins can be epoxidized, in particular olefins with 2 to 6 carbon atoms. The process according to the invention is most particularly suitable for the epoxidation of propene to propene oxide. For economic reasons it would be preferred for an industrial scale process to use propene not in a pure form but as a technical mixture with propane that as a rule contains 1 to 15 vol. % of propane. Propene may be fed as a liquid as well as in gaseous form into the reaction system.

The reaction is preferably carried out in the presence of a solvent in order to increase the solubility of the olefin, preferably propene, in the liquid phase. Suitable as solvent are all solvents that are not oxidized or are oxidized only to a slight extent by hydrogen peroxide under the chosen reaction conditions, and that dissolve in an amount of more than 10 wt. % in water. Preferred are solvents that are completely miscible with water. Suitable solvents include alcohols such as methanol, ethanol or tert-butanol; glycols such as for example ethylene glycol, 1,2-propanediol or 1,3-propanediol; cyclic ethers such as for example tetrahydrofuran, dioxane or propylene oxide; glycol ethers such as for example ethylene glycol monomethyl ether, ethylene glycol monoethyl ether, ethylene glycol monobutyl ether or propylene glycol monomethyl ether, and ketones such as for example acetone or 2-butanone. Methanol is particularly preferably used as solvent.

The olefin is preferably employed in excess relative to the hydrogen peroxide in order to achieve a significant consumption of hydrogen peroxide, the molar ratio of olefin, preferably propene, to hydrogen peroxide preferably being chosen in the range from 1.1 to 30. The solvent is preferably added in a weight ratio of 0.5 to 20 relative to the amount of hydrogen peroxide solution used. The amount of catalyst employed may be varied within wide limits and is preferably chosen so that a hydrogen peroxide consumption of more than 90%, preferably more than 95%, is achieved within 1 minute to 5 hours under the employed reaction conditions.

According to one embodiment of the present invention, reaction conditions like temperature, pressure, selection of olefin and selection of solvent and relative amounts of the components of the reaction mixture are chosen to ensure the presence of only one aqueous liquid phase in which the olefin is dissolved. An additional gaseous olefin containing phase may also be present.

But it is preferred to conduct the epoxidation of olefins with hydrogen peroxide in a multiphase reaction mixture comprising an liquid aqueous hydrogen peroxide rich phase containing an organic solvent having a solubility in water of at least 10% by weight at 25° C. and an liquid organic olefin rich phase. Thereby an even better product selectivity can be achieved.

As will be appreciated by any person skilled in the art, the presence of two immiscible liquid phases in a reaction system comprising an olefin, an water miscible organic solvent and an aqueous hydrogen peroxide solution will depend on many different factors. First of all, the presence of an additional olefin rich liquid organic phase will depend on the temperature and pressure applied in the reactor and the selected olefin. Preferably the applied pressure is at or above the vapor pressure of the olefin at the chosen temperature. Furthermore, it will depend on the selection of the organic solvent. Suitable as organic solvent are all solvents that dissolve in an amount of more than 10 wt. % in water at 25° C. Preferred are solvents that dissolve in an amount of more than 30 wt. % in water at 25° C. preferably more than 50 wt. % in water at 25° C. The most preferred solvents are completely miscible with water. In principle, all solvents as exemplified above can also be used in this preferred embodiment as long as the conditions are met to ensure the presence of two liquid phases.

Additionally, the presence of a second organic olefin rich phase will depend on the relative amounts of olefin, water and solvent. The amount of solvent is chosen to achieve sufficient solubility of the olefin in the hydrogen peroxide rich aqueous phase in order to get the desired rate of reaction. At a given temperature, pressure, olefin and solvent the relative amounts of ingredients can be adjusted to ensure formation of a second liquid organic phase, i.e., to ensure the formation of a second liquid organic olefin rich phase the amount of olefin has to be selected in excess of the amount soluble in the aqueous phase at the chosen temperature and pressure.

A simple means of experimentally confirming the presence of a second liquid organic phase at the reaction conditions is by collecting a sample of the reaction mixture in a container equipped with a sight glass at the temperature and pressure used in the process. Alternatively, the reactor may be equipped with a sight glass at a suitable position to observe the phase boundary directly during the reaction. In case of a continuous flow reactor the sight glass is preferably positioned near the outlet of the reactor effluent to have an optimal control that two liquid phases are present through out the entire residence time within the reactor.

Thus a person skilled in the art can, without any effort, verify whether when applying certain selections for olefins, solvents and reaction parameters a two-liquid phase system as required by the present invention is present and can adjust by variation of the parameters as discussed above in detail the reaction system in order to establish a second liquid organic phase.

According to a most preferred embodiment of the present invention, the olefin is selected to be propene, and methanol is used as a solvent. For example for a reaction mixture comprising propene, methanol, and aqueous hydrogen peroxide at a reaction temperature between 30° C. and 80° C., a pressure from 5 to 50 bar, the ratio of propene flow to total flow in case of a continuous flow system can be adjusted to be in the range of 0.1 to 1, preferably 0.2 to 1 in order to obtain a second liquid organic phase.

An additional gas phase comprising olefin vapor and optionally an inert gas i.e. a gas that does not interfere with the epoxidation can be additionally present according to the present invention. Adding an inert gas is useful to maintain a constant pressure inside the reactor and to remove oxygen gas formed by the decomposition of a small part of the hydrogen peroxide charged to the reactor.

The present invention will be explained in more detail referring to the following examples:

EXAMPLES

EXAMPLE 1

Preparation of an aqueous hydrogen peroxide solution to be used in the process of the present invention.

In a trial plant for the loop process according to the anthraquinone process for the preparation of hydrogen peroxide comprising the steps hydrogenation, oxidation, extraction, drying, and regeneration a working solution comprised of 0.11 mol/l 2-ethyl anthraquinone, 0.29 mol/l 2-ethyl tetra-hydroanthraquinone, 0.13 mol/l 2-isohexyl anthraquinone, and 0.12 mol/l 2-isohexyl tetra-hydroanthraquinone in a solvent mixture comprising 75 vol % of $C_9/C_{10}$ alkyl substituted aryl compounds, and 25 vol % of tris(2-ethyl hexyl) phosphate is used. In the hydrogenation step, a loop reactor was run at a hydrogen pressure of 0.35 MPa and a temperature of 58° C. Palladium black (0.5:1 g/l) was used as hydrogenation catalyst. The hydrogen peroxide equivalent in the hydrogenation was 13.0 g/l.

After the hydrogenation, a part of the hydrogenated working solution is regenerated using active aluminum oxide. Thereafter, the combined working solution is oxidized using the Laporte oxidation as described in G. Goor, J. Glenneberg, S. Jacobi: "Hydrogen Peroxide" Ullmann's Encyclopedia of Industrial Chemistry, Electronic Release, 6$^{th}$ ed. Wiley-VCH, Weinheim Jun. 2000, page 14. Thereafter, the hydrogen peroxide is extracted using deionized water. To the extraction water, 50 ppm $H_3PO_4$ and 20 ppm $HNO_3$ were added, both based on the weight of hydrogen peroxide. The concentration of the extracted aqueous hydrogen peroxide solution was 41%. The working solution was dried by water evaporation in vacuum, and thereafter recycled to the hydrogenation step. The crude hydrogen peroxide solution was stabilized using 200 ppm sodium pyrophosphate based on the weight of hydrogen peroxide and concentrated in vacuum by water evaporation.

The hydrogen peroxide concentration of the solution obtained in this way was 43 wt-%, based on the total weight of the solution, and contained 250 mg/kg $H_2O_2$ phosphates, 20 mg/kg nitrate, and 30 mg/kg of sodium.

EXAMPLES 2–6 AND COMPARATIVE EXAMPLES 1–8

A titanium-silicate catalyst was employed in all examples. The titanium-silicate powder was shaped into 2 mm extrudates using a silica sol as binder in accordance with example 5 in EP 00 106 671.1. The $H_2O_2$ solution according to example 1 was employed after concentrating by water evaporation to 60 wt-%.

Epoxidation is carried out continuously in a reaction tube of 300 ml volume, a diameter of 10 mm and a length of 4 m. The equipment is furthermore comprised of three containers for liquids and relevant pumps and a liquid separating vessel. The three containers for liquids comprised methanol, the 60% $H_2O_2$ and propene. The reaction temperature is controlled via an aqueous cooling liquid circulating in a cooling jacket whereby the cooling liquid temperature is controlled by a thermostat. The reactor pressure was 25 bar absolute. Mass flow of the feeding pumps was adjusted to result in a propene concentration of 38 wt-%, a methanol feed concentration of 48,7 wt-% and an $H_2O_2$ feed concentration of 8 wt-%. Furthermore the feed contained additional components either resulting from the crude $H_2O_2$ (250 mg/(kg $H_2O_2$) phosphate, 20 mg/(kg $H_2O_2$) nitrate, 30 mg/(kg $H_2O_2$) sodium) or were added to the methanol as indicated in Table 1.

When performing the examples and comparative examples, the flow mode was downflow and the cooling jacket temperature was adjusted to 35° C. and the total mass flow was 0.35 kg/h. The product stream was analyzed by gas chromatography and the $H_2O_2$ conversion was determined by titration. $H_2O_2$ selectivity was calculated as the ratio of the amount of propene oxide relative to the total amount of propene oxide and other side-products resulting from $H_2O_2$. The measurements were performed after the running time indicated in Table 1.

TABLE 1

| No. | Amount of components of group iii) added [mg/kg $H_2O_2$] | Amount of components of group iv) [mg/kg $H_2O_2$] | Running time [h] | $H_2O_2$ Conversion [%] | $H_2O_2$ Selectivity [%] |
|---|---|---|---|---|---|
| E2 | — | NH$_3$ 200 | 732 | 94 | 90 |
| E3 | Li 25 | NH$_3$ 500 | 945 | 95 | 90 |
| E4 | — | NH$_3$ 1000 | 47 | 97 | 89 |
| E5 | — | NH$_3$ 1000 | 1114 | 96 | 91 |
| E6 | — | NH$_3$ 1000 | 2356 | 94 | 90 |
| CE1 | Na 170 | 0 | 48 | 98 | 90 |
| CE2 | Na 170 | 0 | 619 | 88 | 75 |
| CE3 | Na 20 + Li 50 | 0 | 745 | 82 | 76 |
| CE4 | Na 20 + Li 50 | 0 | 2184 | 28 | 71 |
| CE5 | Na 20 + Li 100 | 0 | 842 | 85 | 78 |

TABLE 1-continued

| No. | Amount of components of group iii) added [mg/kg $H_2O_2$] | Amount of components of group iv) [mg/kg $H_2O_2$] | Running time [h] | $H_2O_2$ Conversion [%] | $H_2O_2$ Selectivity [%] |
|---|---|---|---|---|---|
| CE6 | Na 20 + Li 100 | 0 | 2134 | 45 | 68 |
| CE7 | Me$_3$N 150 | 0 | 380 | 42 | 74 |
| CE8 | MeNH$_2$ 100 | NH$_3$ 1000 | 2142 | 21 | 82 |

$pk_B$—data for the nitrogen bases published in H. R. Christen; "Grundlagen der organischen Chemie"; Verlag Sauerländer Aarau, Diesterweg Sall Frankfurt am Main; 1975; p. 392 are given in Table 2

TABLE 2

| Bases | $pk_B$ |
|---|---|
| NH$_3$ | 4.76 |
| Me$_3$N (trimethyl amine) | 4.26 |
| MeNH$_2$ (methyl amine) | 3.36 |

When comparing Example 4 with Comparative Example 1 it becomes evident that at the beginning of the continuous process after 48 hours conversion and selectivity is almost identical. This explains why the addition of non-basic salts according to the teaching of EP-A 712 852 and EP-A 757 043 at the short running times disclosed therein leads to acceptable results. But with increasing running time of the process a considerable reduction of conversion and selectivity is observed in Comparative Examples 1–6, whereas in Example 5 even after more than 2300 hours conversion and selectivity is still appropriate. Comparative examples 7 and 8 show that the addition of amine bases having a $pk_B$ of less than 4.5 leads to a tremendous reduction of conversion and selectivity over time.

Further variations and modifications will be apparent to those skilled in the art from the foregoing and are intended to be encompassed by the claims appended hereto.

We claim:

1. A continuous process for the epoxidation of olefins with hydrogen peroxide in the presence of a heterogeneous catalyst promoting the epoxidation reaction, comprising forming an aqueous reaction mixture which comprises:
   i) an olefin;
   ii) hydrogen peroxide;
   iii) less than 100 wppm of a member selected from the group consisting of an alkali metal, an alkaline earth metal, both irrespective whether in ionic or complex form, a base or a cation of a base having a $pk_B$ of less than 4.5, and combinations thereof; and
   iv) at least 100 wppm of a base or a cation of a base having a $pk_B$ of at least 4.5 or combinations thereof, whereby the wppm are based on the total weight of hydrogen peroxide in the reaction mixture, and reacting the reaction mixture in the presence of said heterogeneous catalyst to obtain the desired product.

2. The process of claim 1, wherein the amount of components of group iii) in total is less than 80 wppm based on the total weight of hydrogen peroxide.

3. The process of claim 2, wherein the amount of components of group iii) in total is less than 70 wppm based on the total weight of hydrogen peroxide.

4. The process of claim 2, wherein the amount of components of group iii) in total is less than 60 wppm based on the total weight of hydrogen peroxide.

5. The process of claim 2, wherein the amount of components of group iii) in total is less than 50 wppm based on the total weight of hydrogen peroxide.

6. The process of claim 1, wherein the reaction mixture comprises
   iiia) less than 50 wppm alkali metals, alkaline earth metals or combinations thereof in total, irrespective whether the alkali or alkaline earth metals are present in cationic or complex form; and
   iiib) less than 50 wppm of amines having a $pk_B$ of less than 4.5 or the corresponding protonated compounds in total;
   where the wppm are based on the weight of hydrogen peroxide.

7. The process of claim 1, wherein the amount of components of group iv) in total is 3000 wppm at most based on the total weight of hydrogen peroxide.

8. The process of claim 7, wherein the amount of components of group iv) in total is from 150 to 2000 wppm based on the total weight of hydrogen peroxide.

9. The process of claim 7, wherein the amount of components of group iv) in total is from 200 to 1500 wppm based on the total weight of hydrogen peroxide.

10. The process of claim 7, wherein the amount of components of group iv) in total is from 300 to 1200 wppm based on the total weight of hydrogen peroxide.

11. The process of claim 1, wherein the components of group iv) are selected from the group consisting of organic amines and amides having a $pk_B$ of at least 4.5, organic hydroxylamines having a $pk_B$ of at least 4.5, ammonia and hydroxylamine.

12. The process of claim 1, wherein the reaction mixture further comprises:
   v) at least 100 wppm anions or compounds that can dissociate to form anions in total based on the weight of hydrogen peroxide.

13. The process of claim 1, further comprising performing said process of reacting in a continuous flow reaction system, wherein the reaction mixture is passed through a fixed catalyst bed in down-flow operation mode and reaction heat is at least partially removed during the course of the reaction.

14. The process of claim 13, wherein a fixed bed reactor comprising cooling means is used.

15. The process of claim 14, wherein the fixed bed reactor is a tubular reactor and the cooling means is a cooling jacket.

16. The process of claim 13, wherein the reaction mixture is passed through the catalyst bed with a superficial velocity from 1 to 100 m/h.

17. The process of claim 16, wherein the reaction mixture is passed through the catalyst bed with a superficial velocity from 5 to 50 m/h.

18. The process of claim 16, wherein the reaction mixture is passed through the catalyst bed with a superficial velocity from 5 to 30 m/h.

19. The process of claim 13, wherein the reaction mixture is passed through the catalyst bed with a liquid hourly space velocity (LHSV) from 1 to 20 h$^{-1}$.

20. The process of claim 19, wherein the reaction mixture is passed through the catalyst bed with a liquid hourly space velocity (LHSV) from 1.3 to 15 h$^{-1}$.

21. The process of claim 13, wherein the fixed catalyst bed is maintained in a trickle bed state.

22. The process of claim 21, wherein trickle bed state is, maintained under following flow conditions:

G/λ<2000 m/h and

Lψ<50 m/h, wherein

G is the gaseous superficial velocity defined as the gaseous flow rate in m$^3$/h in the continuous flow reaction system divided by the cross-section of the catalyst bed in m$^2$, L is the liquid superficial velocity defined as the liquid flow rate in m$^3$/h in the continuous flow reaction system divided by the cross-section of the catalyst bed in m$^2$, $$\lambda = \left[\left(\frac{\rho_G}{\rho_W}\right)\left(\frac{\rho_L}{\rho_{Air}}\right)\right]^{1/2}, \text{ and } \psi = \left(\frac{\sigma_W}{\sigma_L}\right) \cdot \left[\left(\frac{\mu_L}{\mu_W}\right)\left(\frac{\rho_W}{\rho_L}\right)^2\right]^{1/3}$$

$\rho_G$ is the density of the gaseous phase in g/cm$^3$, $\rho_L$ is the density of the liquid phase in g/cm$^3$, $\rho_W$ is the density of water in g/cm$^3$, $\rho_{Air}$ is the density of air in g/cm$^3$, $\sigma_W$ is the surface tension of water in dyn/cm, $\sigma_L$ is the surface tension of the liquid phase in dyn/cm, $\mu_L$ is the viscosity of the liquid phase in centipoise, $\mu_W$ is the viscosity of water in centipoise.

23. The process of claim 13, wherein the reaction temperature is from 30 to 80° C.

24. The process of claim 23, wherein the reaction temperature is from 40 to 60° C.

25. The process of claim 24, wherein a temperature profile within the continuous flow reaction system is maintained such that the cooling medium temperature of the cooling means is at least 40° C. and the maximum temperature within the catalyst bed is 60° C. at the most.

26. The process of claim 1, wherein the reaction mixture additionally comprises:

vi) an organic solvent.

27. The process of claim 26, further comprising conducting the reaction in a multiphase reaction mixture comprising an liquid aqueous hydrogen peroxide rich phase containing an organic solvent having a solubility in water of at least 10% by weight at 25° C. and an liquid organic olefin rich phase.

28. The process of claim 26, wherein the organic solvent is methanol.

29. The process of claim 1, wherein a titanium-containing zeolite is used as catalyst.

30. The process of claim 1, wherein the olefin is propene.

31. A continuous process for the epoxidation of propene with hydrogen peroxide in the presence of a titanium-containing zeolite promoting the epoxidation reaction, comprising forming an aqueous reaction mixture which comprises:

i) propene;

ii) hydrogen peroxide;

iii) less than 100 wppm of a member selected from the group consisting of an alkali metal, an alkaline earth metal, both irrespective whether in ionic or complex form, a base or a cation of a base having a pk$_B$ of less than 4.5, and combinations thereof;

iv) at least 100 wppm of a base or a cation of a base having a pk$_B$ of at least 4.5 or combinations thereof; and v) methanol, where the wppm are based on the total weight of hydrogen peroxide in the reaction mixture, and reacting the reaction mixture in the presence of the titanium-containing zeolite to obtain the desired product.

32. A continuous process for the epoxidation of propene with hydrogen peroxide in the presence of a titanium-containing zeolite promoting the epoxidation reaction, comprising forming an aqueous reaction mixture which comprises:

i) propene;

ii) hydrogen peroxide;

iii) less than 100 wppm of a member selected from the group consisting of an alkali metal, alkaline earth metal, both irrespective whether in ionic or complex form, a base or a cation of a base having a pk$_B$ of less than 4.5, or combinations thereof;

iv) at least 100 wppm of a base or a cation of a base having a pk$_B$ of at least 4.5 or combinations thereof; and v) methanol, where the wppm are based on the total weight of hydrogen peroxide in the reaction mixture, and reacting the reaction mixture in a continuous flow reaction system, wherein the reaction mixture is passed through a fixed catalyst bed in down-flow operation mode and reaction heat is at least partially removed during the course of the reaction.

33. The process of claim 32, wherein the fixed catalyst bed is in a tubular reactor and reaction heat is at least partially removed during the course of the reaction by cooling means comprising a cooling jacket.

34. The process of claim 33, wherein the fixed catalyst bed is maintained in a trickle bed state.

35. A continuous process for the epoxidation of propene with hydrogen peroxide in the presence of a titanium-containing zeolite promoting the epoxidation reaction, comprising forming an aqueous reaction mixture which comprises:

i) propene;

ii) hydrogen peroxide;

iii) less than 100 wppm of a member selected from the group consisting of an alkali metal, alkaline earth metal, both irrespective whether in ionic or complex form, a base or a cation of a base having a pk$_B$ of less than 4.5, or combinations thereof;

iv) at least 100 wppm of a base or a cation of a base having a pk$_B$ of at least 4.5 or combinations thereof; and v) methanol, where the wppm are based on the total weight of hydrogen peroxide in the reaction mixture, and reacting the reaction mixture in a multiphase reaction mixture comprising an liquid aqueous hydrogen peroxide rich phase containing methanol and an liquid propene rich phase.

36. The process of claim 35, further comprising reacting the reaction mixture in a continuous flow reaction system, wherein the reaction mixture is passed through a fixed catalyst bed in down-flow operation mode and reaction heat is at least partially removed during the course of the reaction.

37. The process of claim 36, wherein the fixed catalyst bed is in a tubular reactor and reaction heat is at least partially removed during the course of the reaction by cooling means comprising a cooling jacket.

38. The process of claim 36, wherein the fixed catalyst bed is maintained in a trickle bed state.

* * * * *